(12) United States Patent
Vyskocil et al.

(10) Patent No.: US 9,416,030 B2
(45) Date of Patent: Aug. 16, 2016

(54) METHOD FOR TREATMENT OF PROCESS WATER

(71) Applicant: AVA-CO2 Schweiz AG, Zug (CH)

(72) Inventors: Jan Vyskocil, Zug (CH); Stephan Koehler, Zug (CH); François Badoux, Rotkreuz (CH)

(73) Assignee: AVA-CO2 Schweiz AG, Zug (CH)

( * ) Notice: Subject to any disclaimer, the term of this patent is extended or adjusted under 35 U.S.C. 154(b) by 0 days.

(21) Appl. No.: 14/565,673

(22) Filed: Dec. 10, 2014

(65) Prior Publication Data

US 2016/0060141 A1  Mar. 3, 2016

(30) Foreign Application Priority Data

Aug. 26, 2014 (DE) .......................... 10 2014 112 240

(51) Int. Cl.
| | | |
|---|---|---|
| *C02F 1/44* | (2006.01) | |
| *C10L 9/08* | (2006.01) | |
| *B01D 63/00* | (2006.01) | |
| *C07C 51/47* | (2006.01) | |
| *C07D 307/48* | (2006.01) | |
| *B01D 61/14* | (2006.01) | |
| *C02F 1/26* | (2006.01) | |
| *C02F 103/36* | (2006.01) | |
| *C02F 101/34* | (2006.01) | |

(52) U.S. Cl.
CPC ................ *C02F 1/44* (2013.01); *B01D 61/142* (2013.01); *B01D 63/00* (2013.01); *C07C 51/47* (2013.01); *C07D 307/48* (2013.01); *C10L 9/086* (2013.01); *B01D 2311/263* (2013.01); *B01D 2313/38* (2013.01); *B01D 2315/16* (2013.01); *B01D 2317/02* (2013.01); *B01D 2317/022* (2013.01); *B01D 2317/025* (2013.01); *C02F 1/26* (2013.01); *C02F 2101/34* (2013.01); *C02F 2103/365* (2013.01)

(58) Field of Classification Search
CPC .......................................................... C02F 1/44
USPC .......................................................... 549/483
See application file for complete search history.

(56) References Cited

FOREIGN PATENT DOCUMENTS

| | | |
|---|---|---|
| DE | 10 2009 027 007 A1 | 12/2010 |
| DE | 20 2012 100 129 U1 | 4/2012 |
| DE | 10 2011 053 034 A1 | 2/2013 |
| DE | 10 2012 002 590 A1 | 8/2013 |

*Primary Examiner* — Taofiq A Solola
(74) *Attorney, Agent, or Firm* — Collard & Roe, P.C.

(57) ABSTRACT

Within the scope of hydrothermal carbonization of biomass, not only the main product, coal, but also the platform chemical 5-hydroxymethyl furfural, as well as furfural and levulinic acid, are formed. These are extracted from the process water of the carbonization reaction. However, in this connection, the problem exists that humic substances deposit on the container walls of the extraction column and can only be removed again by means of great cleaning effort. Furthermore, oligomers clearly worsen the purity of the product. This problem is solved by a filtration cascade through which the process water passes before extraction. In this connection, first the impurities mentioned are removed in a first filtration stage, and the remaining products and educts are separated from one another in a second filtration stage. Only the products are passed to extraction.

8 Claims, 1 Drawing Sheet

METHOD FOR TREATMENT OF PROCESS WATER

CROSS REFERENCE TO RELATED APPLICATIONS

Figure 1:
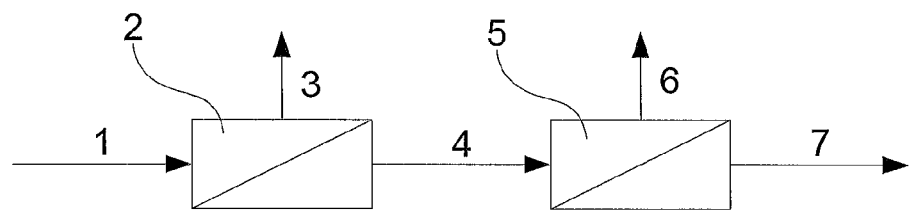

Applicant claims priority under 35 U.S.C. §119 of German Application No. 10201411240.2 filed on Aug. 26, 2014, the disclosure of which is incorporated by reference.

The present invention relates to a method for treatment of process water, particularly in advance of extraction of the reaction products.

Within the scope of hydrothermal carbonization, biomass is carbonized in a reaction container, with the addition of steam, in a temperature range of about 150-230° C. and at an elevated pressure of about 4-28 bar. Aside from the bio-coal that results in this way, other products also occur during this process, such as particularly the basis chemicals 5-hydroxymethyl furfural, furfural, and levulinic acid. These are extracted from the process water during a downstream step; the process water passes through an extraction column for this purpose.

Aside from the actually desired carbonization reaction, however, many different secondary reactions occur, so that aside from the desired products, a number of humic substances and oligomers are formed. In this connection, oligomers are small, branched chains composed of individual monomers of the products. Because of their method of formation, they have a great similarity with the products in terms of their physical and chemical properties, and cannot be separated from the products during the subsequent process steps, or can be separated only with difficulty, and thereby lead to a reduction in product purity. Just like the humic substances that are also formed, the oligomers therefore represent impurities in the extraction, whereby clearly more humic substances occur. The humic substances can occur both in dissolved and non-dissolved form, whereby the non-dissolved part leads to reduction in throughput and contaminants as the result of deposition during cooling in the heat exchanger, so that in part, the production process of the products must be interrupted for cleaning of the heat exchanger. The dissolved portions, in contrast, disrupt the further process steps of product isolation, in other words, in particular, extraction of the products. They deposit on the walls and separation apparatuses of the extraction columns and therefore require a high level of cleaning effort, in order to keep the systems in operation.

Against this background, the present invention is based on the task of keeping the cleaning effort for the extraction columns low and, at the same time, of improving product purity and thereby increasing the quality of the product, in other words of the 5-hydroxymethyl furfural, the furfural, and the levulinic acid.

This is accomplished by means of a method for treatment of process water of a hydrothermal carbonization process in accordance with the characteristics of claim 1. Further practical embodiments of such a method can be derived from the dependent claims.

According to the invention, for this purpose the process water is passed through a filter cascade, which has multiple filtration stages, before entry into the extraction column. In each filtration stage, the components in the process water, of which the size of the individual particles exceeds the permeability of the filtration stage, in each instance, are eliminated. Thus, the separation means in the first filtration stage are selected so that essentially the impurities, in other words the humic substances and the oligomers, are retained as a retentate. The products 5-hydroxymethyl furfural, furfural, and levulinic acid continue to be contained in the permeate that represents the main stream, along with the educts such as fructose or glucose, for example. This particularly holds true for liquid educts. To the extent that solid educts, such as topinambur or wood chips, for example, are used, these remain in the reactor.

In a second filtration stage, to which the permeate of the first filtration stage is passed as a feed stream, the separation means are once again selected in such a manner that the educts, in other words essentially fructose and glucose, are retained as a second retentate, while a second permeate more or less now contains only the products 5-hydroxymethyl furfural, furfural, and levulinic acid, as well as all the substances that once again are smaller than these.

By means of this method of procedure, multiple problems are solved at the same time. The humic substances that dirty the extraction columns and therefore lead to great effort and expenditure are eliminated by the first filtration. Likewise, the oligomers, which would contaminate the product, are eliminated within the scope of the first filtration. The fructose and/or glucose separated out in the second step can be passed back into the method, in other words placed in the reactor, and there can improve the yield in a further pass.

With some advantage, further separation of the second permeate can possibly take place by means of further filtration stages, so that filtration takes place one stage after another, by using a separation means, in which the permeability of one filtration stage lies once just above the size of the products and the permeability of another filtration stage lies once just below the size of the products, so that precise filtration of individual products can take place. In this connection, the molecule size is the deciding factor, in each instance.

The same method of procedure can be followed for the second retentate, as well. Within this filtration cascade that has been shown, the last separation stage has the task of increasing the concentration of the products or educts by means of carrying away reaction water. By means of this step, the subsequent extraction can be carried out more efficiently. The permeates formed are particularly suitable for being passed back to an earlier filtration stage within the cascade, so that in these, no additional substances, such as dissolved salts, organic substances or bacteria, for example, are introduced into the system and thereby increase the degree of purity once again.

Preferably, membrane filters are provided as separation means in the individual filtration stages; particularly preferably, these are solution/diffusion membranes and/or ion-selective membranes such as anion exchanger membranes or cation exchanger membranes, because in this way, the yield can be improved, with simultaneous reduction of operating substances and ancillary substances.

Furthermore, it has been proven to be practical to keep the inflow of process water and/or permeate to a filtration stage uniform, and thereby to ensure that the inflow more or less corresponds to the outflow.

Since the process water as it is directly taken from the reactor of the hydrothermal carbonization also contains the bio-coal that has formed, it is furthermore practical to pass the process water to a separate solid/liquid filtration stage before entry into the first filtration stage. For this purpose, surface or depth filtration, particularly preferably membrane filtration, is carried out here, as well.

The invention described above will be explained in greater detail below, using an exemplary embodiment.

Figure 2:
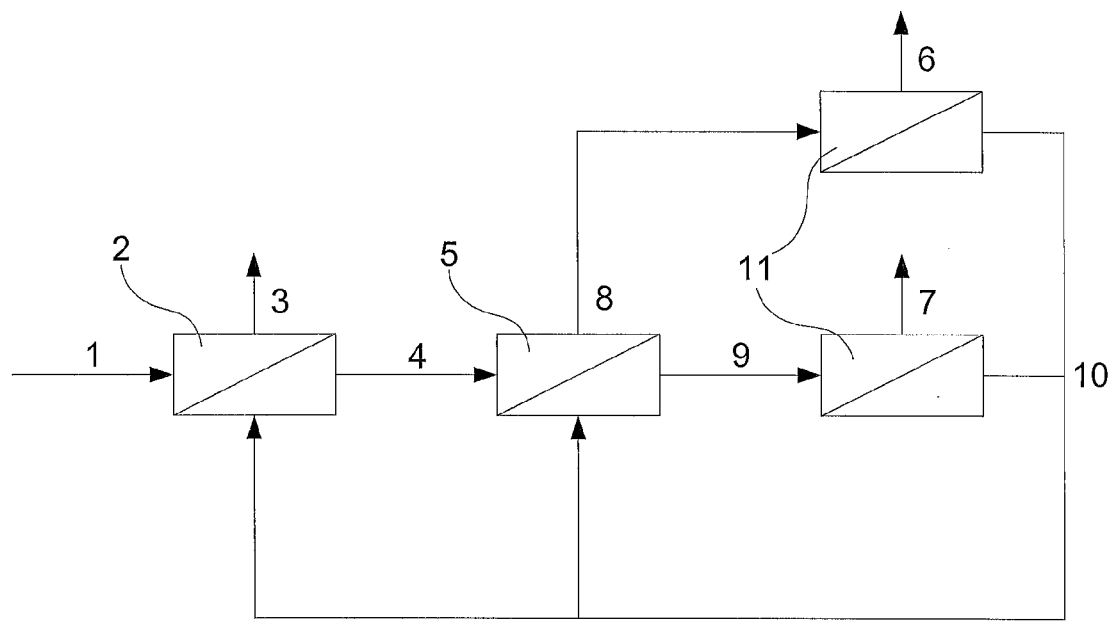

The drawing shows:

FIG. 1 a simple filter cascade having two filter stages, in a schematic representation, and FIG. 2 an expanded filter cascade having three filter stages, in a schematic representation.

FIG. 1 shows a simple filter cascade with which incoming process water 1 from the hydrothermal carbonization process is supposed to be pretreated before entry into the extraction column. At the point in time being observed, the process water 1 has already passed through a solid/liquid filtration, which is not of any great interest here and therefore has not been shown in the drawing, and enters into a first filtration stage 2 in this situation. This is a membrane filtration stage, the permeability of which is structured in such a manner that impurities 3 such as humic substances or oligomers are retained in the first filtration stage 2 as a retentate, while products 7 and educts 6, in other words 5-hydroxymethyl furfural, furfural, and levulinic acid, on the one hand, and sugar, sugar derivatives, and, in this connection, in particular, fructose, on the other hand, pass through the first filtration stage 2 in a first permeate 4. The impurities 3 are conducted away from the first filtration stage 2 and passed to further use or disposal. The first permeate 4, which contains the educts 6 and the products 7, is then passed to a second filtration stage 5, which also represents a membrane filtration stage. The permeability of this second filtration stage 5, however, is selected in such a manner that the educts 6 are retained, while the products 7 can once again pass through the second filtration stage 5. In this case, the educts 6 are retained as a retentate and passed back into the process of hydrothermal carbonization, for example. The second permeate with the products 7 can now be passed to the extraction column.

FIG. 2 shows an alternative to the filter cascade shown in FIG. 1, in which not only the second retentate 8 but also the second permeate 9 are passed to a renewed further filtration stage 11. By means of the renewed filtration, up-concentration of the desired substances takes place, so that the subsequent processes take place more effectively, and therefore the extraction columns can work more effectively with regard to the products 7. In this connection, the further permeates 10 from the further filtration stages 11 are furthermore passed to the earlier filtration stages, in other words the first filtration stage 2 and the second filtration stage 5, and thereby bring with them a washing-out effect as support for the separation process by means of diafiltration.

Therefore, a method for treatment of process water of a hydrothermal carbonization process has been described above, in the course of which method the process water that occurs in the hydrothermal carbonization process is filtered in such a manner that greater product purity and, at the same time, a lower degree of contamination occurs for the systems in question, and thereby the efficiency of the method is clearly improved.

REFERENCE SYMBOL LIST 1 process water
2 first filtration stage
3 impurities
4 first permeate
5 second filtration stage
6 educts
7 products
8 second retentate
9 second permeate
10 further permeate
11 further filtration stage

The invention claimed is:

1. A method for treatment of process water of a hydrothermal carbonization process, wherein, in a first filtration stage, the process water is separated by means of a first membrane filter into a first retentate that essentially contains humic substances and/or oligomers and a first permeate that essentially contains products comprising 5-hydroxymethyl furfural and/or furfural and/or levulinic acid, and educts comprising glucose and/or fructose, and the first permeate is passed to a second filtration stage, in which the first permeate is separated by means of a second membrane filter into a second retentate that essentially contains glucose and/or fructose and a second permeate that essentially contains 5-hydroxymethyl furfural and/or furfural and/or levulinic acid, after which the second permeate is passed to an extraction step in an extraction column for extraction of the 5-hydroxymethyl furfural and/or furfural and/or levulinic acid.

2. The method according to claim 1, wherein the second permeate is passed to at least one further filtration stage before being passed to the extraction step or to an alternative further use, in which stage the second permeate is separated into further permeates that contain different individual products, and further retentates.

3. The method according to claim 1, wherein the second retentate is up-concentrated in at least one further filtration stage.

4. The method according to claim 1, wherein the permeates of the last filtration stage or filtration stages are passed to earlier filtration stages as an inflow.

5. The method according to claim 1, wherein the filtration stages that follow one another differ in that they retain molecules of an increasingly smaller size.

6. The method according to claim 1, wherein the inflow of process water and/or permeate to a filtration stage takes place in uniform manner.

7. The method according to claim 6, wherein the inflow of process water and/or permeate to a filtration stage is adjusted in such a manner that the outflow amount at most corresponds to the inflow amount.

8. The method according to claim 1, wherein the process water is passed to a separate solid/liquid filtration stage before entry into the first filtration stage.

\* \* \* \* \*